US008424532B2

(12) United States Patent
Esquivel et al.

(10) Patent No.: US 8,424,532 B2
(45) Date of Patent: Apr. 23, 2013

(54) CRANIAL SURGICAL DRAPE

(75) Inventors: Debbie S. Esquivel, Lindenhurst, IL (US); Fred L. Allen, Wonder Lake, IL (US); Kimberly M. Haines, Deerfield, IL (US); Angelique M. Trichak, Chicago, IL (US)

(73) Assignee: Medline Industries, Inc., Mundelein, IL (US)

( * ) Notice: Subject to any disclaimer, the term of this patent is extended or adjusted under 35 U.S.C. 154(b) by 40 days.

(21) Appl. No.: 12/843,603

(22) Filed: Jul. 26, 2010

(65) Prior Publication Data

US 2012/0017921 A1 Jan. 26, 2012

(51) Int. Cl.
*A61B 19/08* (2006.01)

(52) U.S. Cl.
USPC .......................................... 128/853; 128/849

(58) Field of Classification Search .................. 128/849, 128/853, 850–852, 854–855
See application file for complete search history.

(56) References Cited

U.S. PATENT DOCUMENTS

| | | | | |
|---|---|---|---|---|
| 3,721,242 | A * | 3/1973 | Krusko | 604/365 |
| 3,791,381 | A * | 2/1974 | Krzewinski | 128/855 |
| 3,799,161 | A * | 3/1974 | Collins | 128/854 |
| 4,089,331 | A * | 5/1978 | Hartigan et al. | 128/850 |
| 4,559,937 | A * | 12/1985 | Vinson | 604/356 |
| 5,464,024 | A * | 11/1995 | Mills et al. | 128/849 |
| 5,778,889 | A * | 7/1998 | Jascomb | 128/849 |
| 6,213,124 | B1 * | 4/2001 | Butterworth | 128/849 |
| 6,725,864 | B2 * | 4/2004 | Ewonce et al. | 128/849 |

* cited by examiner

*Primary Examiner* — Patricia Bianco
*Assistant Examiner* — Camtu Nguyen
(74) *Attorney, Agent, or Firm* — McAndrews, Held & Malloy, Ltd.

(57) ABSTRACT

A drape for use in cranial surgical procedures including a sterile sheet and a plurality of fluid-collection reservoirs surrounding a cranial region fenestration. The drape further can include a thoracic region fenestration for concurrent or directly subsequent thoracic surgical procedures. Advantageously, the drape allows for a superior aseptic surgical field and superior drainage facilitated by a multi-pouch configuration.

13 Claims, 2 Drawing Sheets

11 3 9 7 8 12 6 14 1 13 10 2 B 15 5 A C 4

CRANIAL SURGICAL DRAPE

RELATED APPLICATIONS

This application does not claim priority to any preceding application or patent.

FIELD OF INVENTION

The present technology, in general, relates to a cranial surgical drape. More particularly, the present technology relates to a cranial surgical drape with a fluid-collection pouch reservoirs which reduces potential surgical field contamination and effectively collects any irrigating and bodily fluids. Moreover, the cranial surgical drape has an additional opening for thoracic procedures and other features that facilitate cranial surgical procedures.

BACKGROUND OF INVENTION

A patient undergoing a surgical procedure is generally at least partially covered by a surgical drape. The surgical procedure is often performed through a fenestration (which can be a window, slit, or other opening) in the drape. The importance of surgical draping in providing an aseptic field about the central operative area is well known. It is common practice for many types of surgery to cover the patient and operating table with a sterile drape in such a way that only the portion of the body upon which surgery is to be performed is presented to the surgeon. The drape must conform rather closely to the contour of the operative area to insure that a sterile surgical field is maintained until the procedure is completed. One of the objectives of some surgical drapes is to disperse fluid runoff from the surgical site so that it does not obstruct the working of the surgeon and so that it does not soil the patient. It is presently common practice to furnish or employ various types of drape constructions and draping procedures for different types of surgical procedures.

Certain types of surgeries result in only a small amount of fluid runoff from the surgical site. In these cases, the fluid may be simply dispersed across the surface of the drape; some drapes are produced with an absorbent exterior surface in order to absorb such fluid runoff. In contrast to those types of surgeries, cranial surgeries often result in a substantial amount of fluid runoff from the surgical site. In cranial surgical cases, the surgical drape is used to channel these fluids into a receptacle. One such receptacle is a pouch attached to the exterior of the surgical drape. Drapes with such receptacles are disclosed in U.S. Pat. Nos. 4,890,628, 4,598,458, 4,559,937, 4,323,062, 4,169,472, 3,955,569, 3,952,738, 3,911,912, and 3,791,382. However, due to the single drainage avenue for fluid collection, the surgeon is often forced to re-adjust the drape or channeling means such that the fluids drain into the receptacle.

Certain cranial surgeries require the surgeon to remove a portion of the skull. This extracted cranial bone may be re-implanted in the patient's skull at a later date. Current procedures include removing the cranial bone in a sterile fashion and freezing it in a deep-freezer for re-implantation at a later date. This practice presents various risks when a specimen is removed from the patient; handled and wrapped for future sterile, aseptic re-introduction; and then re-introduced to a sterile field some time after harvesting. The technical requirements for monitoring and preserving the cranial bone ex-vivo are demanding due to risks of contamination and specimen deterioration. One current technique to avoid monitoring and preserving ex-vivo samples is to implant the cranial bone into the patient's own abdomen directly after extraction. This implantation allows for the cranial bone to remain in a sterile environment and with the patient until re-implantation is warranted.

BRIEF SUMMARY OF THE INVENTION

The present technology generally relates to a surgical drape used during aseptic surgical procedures. More particularly, the present technology relates to a surgical drape ideal for cranial surgeries, though the present technology may be adapted for drapes for other types of surgical procedures. The present technology provides for a superior aseptic surgical field and superior drainage facilitated by a plurality of fluid-collection reservoirs (or a plurality of fluid-collection pouches) adjacent to the surgical site.

The cranial surgical drape comprises a cranial region fenestration that enables the surgeon access to the incision and surgical site. Further, the cranial surgical drape has a fluid collection pouch 10 having multiple reservoirs 11, 12 and 13 designed to collect irrigating or bodily fluids which emanate from the surgical site. In a preferred embodiment of the cranial surgical drape, an additional thoracic region fenestration is present for a concurrent, or directly subsequent, thoracic surgical procedure.

As one aspect of the present invention, a cranial surgical drape to cover a patient during surgery is provided. The drape comprises a sheet 15 having an interior surface for contacting the cranial region of a surgical patient and an exterior surface for facing away from the patient after placement. The drape also comprises a fenestration in the cranial region, wherein the sheet 15 has a perimeter that defines the fenestration. The drape further comprises a fluid-collection pouch on the exterior surface of the sheet adjacent to and surrounding a majority of the perimeter of the cranial region fenestration. The fluid-collection pouch is fastened to the exterior surface and is in fluid communication with the cranial region fenestration.

As another aspect of the present invention, a cranial surgical drape to cover a patient during surgery is provided. The drape comprises a sheet 15 (as described above), a fenestration in the cranial region of the sheet, and a fenestration in the thoracic region of the sheet 15. The sheet 15 has first and second perimeters that defines the fenestrations. The drape also includes a fluid-collection pouch on the exterior surface of the sheet surrounding and adjacent the fenestration in the cranial region fastened to the exterior surface and in communication with said fenestration in the cranial region.

As yet another aspect of the present invention, a cranial surgical drape to cover a patient during surgery is provided. The drape comprises a sheet 15 having an interior surface for contacting the cranial region of a surgical patient and an exterior surface for facing away from the patient after placement. The drape also comprises a fenestration in the cranial region, wherein the sheet 15 has a perimeter that defines the fenestration. The drape also includes a fluid-collection pouch on the exterior surface of the sheet adjacent to and surrounding a majority of the perimeter of the cranial region fenestration, wherein the fluid-collection pouch is fastened to the exterior surface and is in fluid communication with the cranial region fenestration. The fluid-collection pouch comprises at least three reservoirs 11, 12, 13 and each of the reservoirs is on a different side of the cranial region fenestration. The drape also include a malleable strip 14 at a top opening of the reservoir 11 adapted for to maintaining the reservoir in an open configuration. A fenestration is provided in the thoracic region, wherein the sheet 15 has a perimeter that defines the fenestration. The drape also comprises adhesive on the interior surface surrounding the cranial region and thoracic region fenestrations. The drape also includes one or more cord fasteners.

As yet another aspect of the present invention, a packaged sterile surgical drape is provided. The packaged sterile surgical drape comprises a drape according to any of the embodiments described herein and a package that contains the sterile surgical drape and maintains the sterility of the drape. In this aspect, the drape is a sterile drape.

In the various aspects and embodiments of the cranial surgical drapes described herein, the fluid-collection pouch may comprise a plurality of reservoirs. When the drape has a single fluid-collection pouch with multiple reservoirs, it is desirable to have a reservoir on different sides of the fenestration, preferably on at least three sides of the fenestration. Alternatively, a drape may include a plurality of fluid-collection pouches, and it may be desirable to have each of the fluid-collection pouches on a different side of the fenestration.

The present surgical drapes can include an absorbent layer on the exterior surface, such as in a middle portion of the exterior surface. The absorbent layer can comprise any absorbent material suitable for a surgical drape, though pulp-based non-woven fabric is presently preferred. The drape can include any suitable material, such as spunbond polypropylene.

In the present surgical drapes, the fluid-collection pouch can contain a filter. The drapes can also include one or more cord fasteners and/or one or more channels to provide fluid communication between the fenestration and the fluid-collection pouch.

DETAILED DESCRIPTION OF THE INVENTION

Figure 1:
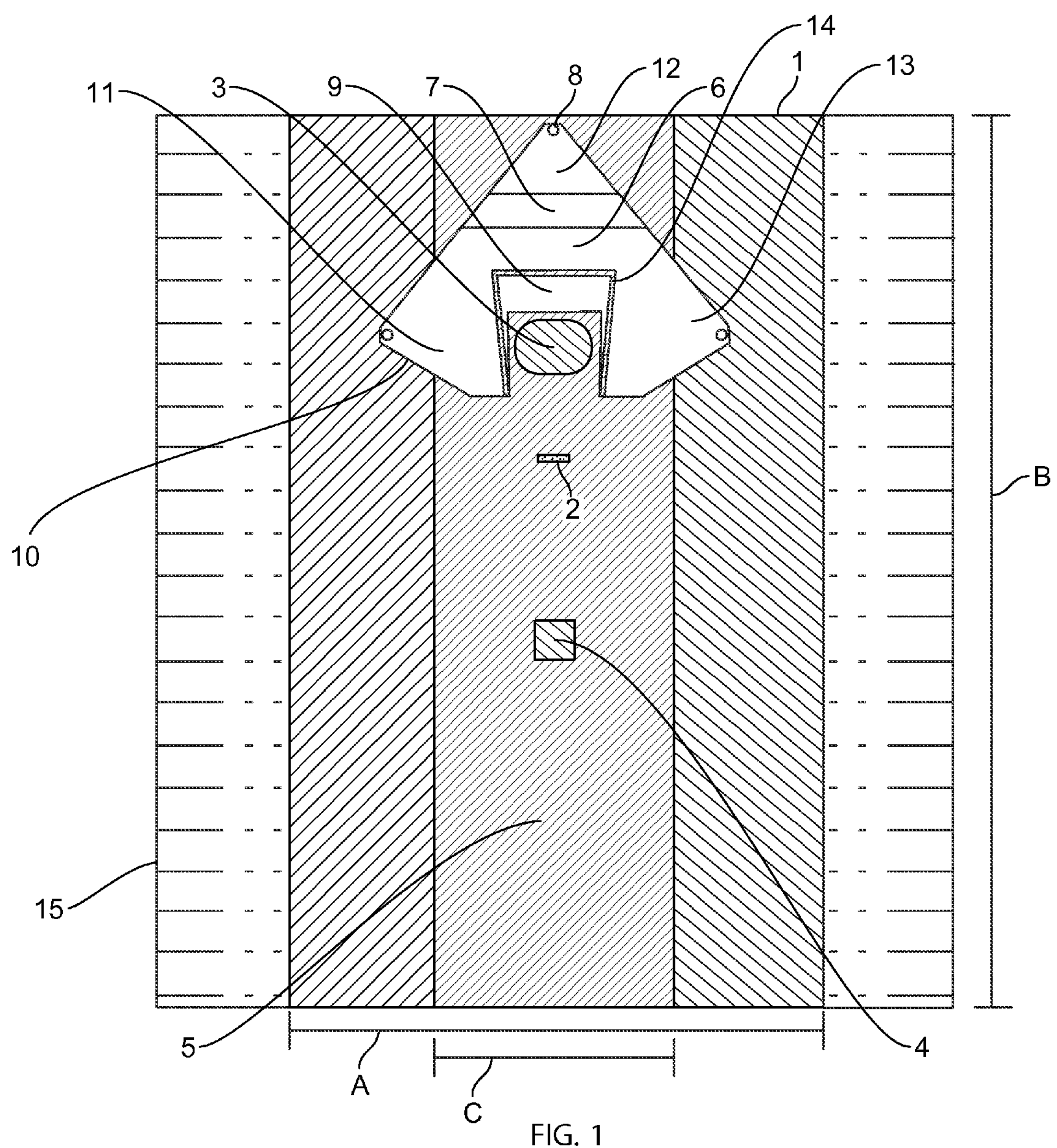
FIG. 1 shows the one embodiment of the cranial surgical drape laid flat and viewing the exterior surface. One pouch with three triangular reservoirs surrounds a majority of the perimeter of the fenestration and is adjacent to the cranial region fenestration. A cord fastener on the exterior surface of the cranial surgical drape can be used at the discretion of the surgical team for uses including, but not limited to, fastening irrigation hose(s) and/or medical monitoring equipment. A filter is shown here which inhibits solids from reaching the bottom of the fluid-collection reservoir. The fluid-collection pouch shown here contains three access ports located in each fluid-collection reservoir at the furthest distance from the cranial region fenestration. Each port is sealed with a cap. A thoracic region fenestration is located directly below the cranial region fenestration on the longitudinal axis of the drape.

The present inventors have recognized the desirability of a cranial surgical drape which allows the surgeon a sterile operating field and without need to re-adjust the drape for fluid collection. Additionally, a single drape with multiple fenestrations enables the surgeon to maintain two aseptic surgical fields—one for cranial procedures and one for thoracic procedures—during one anesthetic session. The present cranial surgical drape is designed to lay over the patient in a longitudinal orientation. The drape is designed to be positioned once at the beginning of the surgical procedure and not be re-adjusted through the course of the procedure.

In the present drawings, like reference characters are utilized to identify like parts throughout several views.

FIG. 1 illustrates a cranial surgical drape 1 which is particularly adapted for use in craniotomy surgical procedures. Both the interior and exterior surfaces of the drape may comprise a polypropylene, or a pulp-based non-woven fabric or another material suitable for a surgical drape. Preferably, the drape comprises spunbond polypropylene (which is also known as SMS in the industry). Spunbond polypropylene provides the patient with more comfort compared to other polypropylenes.

Figure 2:
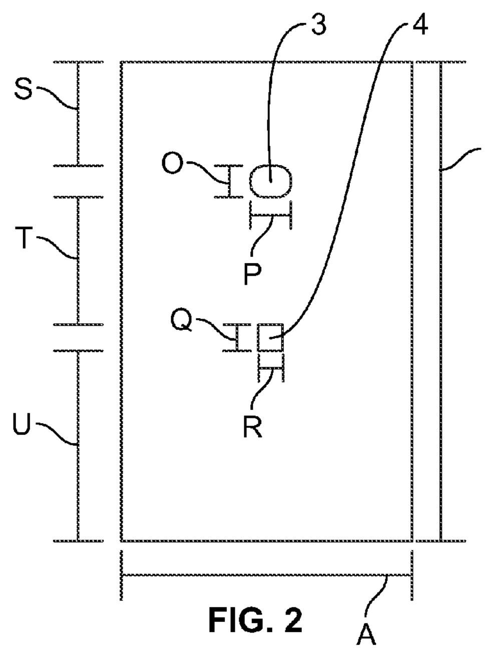
FIG. 2 shows the cranial region fenestration and the thoracic region fenestration in the cranial surgical drape.

FIG. 2 shows a cranial surgical drape with two fenestrations. The cranial surgical drape 1 can have certain length B and width A dimensions. In some embodiments of the present surgical drape, the drape dimensions can be about 100 to about 170 inches long B and about 60 to about 100 inches wide A, alternatively about 110 to about 160 inches long B and about 65 to about 95 inches wide A, alternatively about 120 to about 150 inches long B and about 70 to about 90 inches wide A, alternatively about 130 to about 140 inches long B and about 75 to about 85 inches wide A, alternatively about 135 inches long B and about 80 inches wide A.

The shape of the fenestrations in the cranial surgical drape is not limited. Preferably, the cranial region fenestration 3 is oval. Preferably, the thoracic region fenestration 4 is rectangular. On the interior surface surrounding the cranial region and thoracic region fenestrations, an adhesive can be provided which can be applied to the patient's body. Thus, the present drapes can comprise an adhesive layer on the interior surface of the drape surrounding the cranial region fenestration and/or the thoracic region fenestration. When the adhesive is applied to the patient's body, this insures the drape remains closely to the contour of the operative area resulting in the sterile field being maintained until the procedure is completed.

In a preferred embodiment, an absorbent layer 5 extends longitudinally in a middle region of the drape. Preferably, the absorbent layer is comprised of a pulp-based non-woven.

Figure 4:
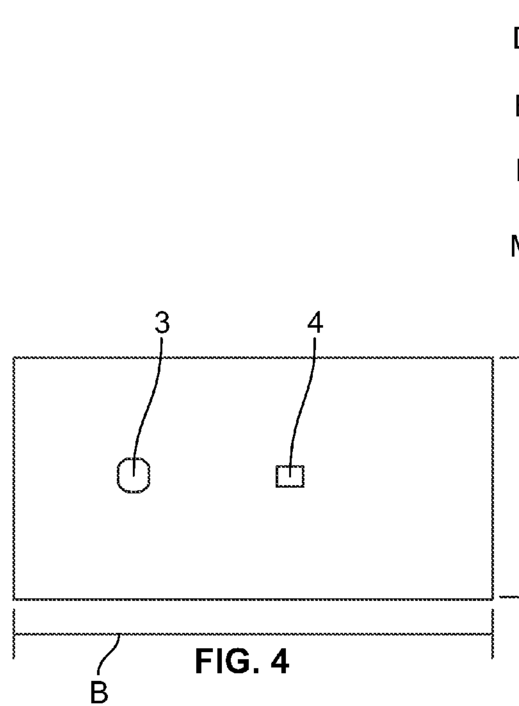
FIG. 4 shows an absorbent layer which may be present in the middle of the exterior extending parallel to the longitudinal axis.

FIG. 4 shows the absorbent layer of the cranial surgical drape with two fenestrations. The absorbent layer 5 can have certain length B and width C dimensions. The absorbent layer dimensions can be about 100 to about 170 inches long B and about 10 to about 60 inches wide C, alternatively about 110 to about 160 inches long B and about 20 to about 50 inches wide C, alternatively about 120 to about 150 inches long B and about 25 to about 45 inches wide C, alternatively about 130 to about 140 inches long B and about 30 to about 40 inches wide C, alternatively about 135 inches long B and about 36 inches wide C. The cranial region fenestration 3 can have certain length O and width P dimensions. The length O can be between about 2 to about 14 inches, alternatively between about 4 and about 12, alternatively about 2 to about 10 inches; preferably, the length O is about 8 inches in length. The width P can be between about 6 to about 18 inches, alternatively between about 8 and about 16 inches, alternatively about 10 to about 14 inches; preferably, the width P is about 12 inches. The thoracic region fenestration 3 can have certain length Q and width R dimensions. The length Q can be between about 1 to about 12 inches, alternatively between about 2 and about 10 inches, alternatively about 4 to about 8 inches; preferably, the length Q is about 6 inches. The width R can be between about 1 to about 12 inches, alternatively between about 2 and about 10 inches, alternatively about 4 to about 8 inches; preferably, the width P is about 6 inches. The distance from the thoracic region fenestration to the terminus of the drape designed to cover the patient's feet U can be between about 35 and about 75 inches in length, alternatively between about 40 and about 70 inches, alternatively between about 45 and about 65 inches, alternatively between about 50 and about 60 inches; preferably, the distance U is about 53 inches. The distance between the cranial region fenestration and the thoracic region fenestration T can be between about 25 and about 50 inches in length, alternatively about 30 and about 45 inches, alternatively about 35 and about 40 inches; preferably, the distance T is about 37 inches. The distance from the cranial region fenestration to the end of the drape designed to lie over the patient's head S can be between about 20 and about 45 inches in length, alternatively about 25 to about 40 inches, alternatively about 30 to about 35 inches; preferably, the distance S is about 31 inches in length.

In another preferred embodiment, the cranial surgical drape may contain a cord fastener 2 to secure medical equipment, including, but not limited to irrigation tubes or medical monitoring equipment. The cord holder can be comprised of a clip, hook, snap, or strap; preferably, the cord holder is comprised of a Velcro strap.

Figure 3:
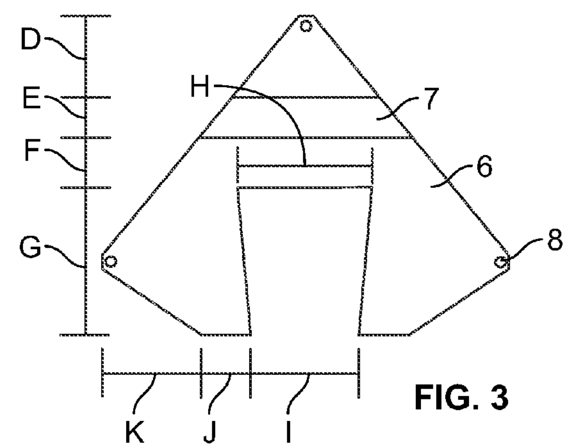
FIG. 3 shows the front view of a fluid-collection pouch with three reservoirs without the cranial surgical drape or cranial region fenestration.
Figure 5:
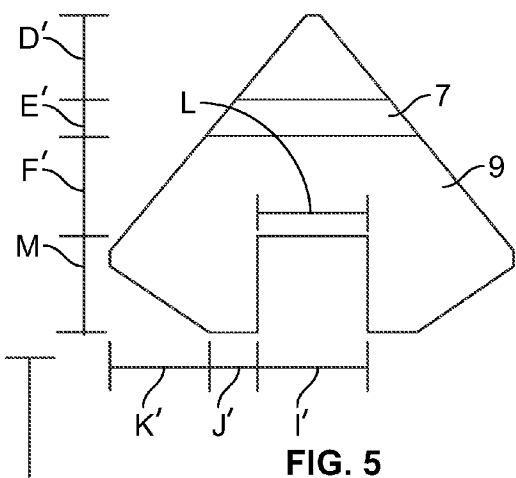
FIG. 5 shows the back view of a fluid-collection pouch with three reservoirs without the cranial surgical drape or cranial region fenestration.

FIG. 3 shows the front panel of a fluid collection pouch. FIG. 5 shows the back panel of a fluid-collection pouch 10. The fluid-collection pouch 10 can be of any shape capable of holding fluid. Preferably, the fluid-collection pouch 10 is rectangular. More preferably, the fluid collection pouch 10 is triangular.

The fluid collection pouch 10 comprises a front panel 6 and a back panel 9 joined along common side edges and defining a one or more fluid receiving reservoirs 11, 12 and 13 therein with the open end positioned adjacent the cranial region fenestration 3. The one or more pouches should be arranged in an orientation such that the majority of the perimeter of the cranial region fenestration is bordered by one or more fluid-collection pouch openings. The fluid collection pouch is preferably constructed of a flexible, fluid-impervious material such as a plastic film. Most preferably, the fluid-collection pouch 10 is constructed of polyethylene. It is preferred that the pouch is made of a substantially clear material to allow inspection of collected fluid through the pouch material. The pouch is attached to the exterior surface with adhesive. Heat-activated sealants are also contemplated to secure the pouches to the exterior surface. The sides of the pouch are sealed, preferably either by heat or adhesive. Sides are preferably sealed such that pouch tapers such that the corners forming each reservoir is narrower than the top opening of the pouch. The plastic or other impervious material should be able to withstand the temperatures and gases used during the sterilization process which includes temperatures in excess of 140° F. for ethylene oxide sterilization. A preferred method of sterilizing the cranial surgical drape is ethylene oxide sterilization. A particularly well suited film material for ethylene oxide sterilization is polyethylene. With steam sterilization, the plastic selected must be able to withstand temperatures in the range from 250° to 270° F.

In FIGS. 3 and 5, numerous measurements are listed to best describe how elements of the fluid-collection pouch are orientated. The length D represents the distance between the bottom of the center fluid-collection reservoir and the top of the fluid-collection opening. D and D' may or may not be the same length. Preferably, D and D' can be between about 4 and about 20 inches in length, alternatively from about 9 inches to about 12 inches in length. Most preferably, D and D' are about 10.5 inches in length. The length E represents the depth measurement of the filter within the fluid-collection pouch. E and E' may or may not be the same length. Preferably, E and E' can be between about 1 and about 10 inches in length, alternatively from about 4 inches to about 6 inches. Most preferably, E and E' are about 5 inches in length. The length F represents the distance between the top of the fluid-collection opening and the filter. F and F' may or may not be the same length. Preferably, F and F' can be between about 1 and about 10 inches in length, alternatively from about 4 inches to about 6 inches. The length I represents a portion of the fluid-collection pouch where one of the reservoirs is located. I and I' may or may not be the same length. Preferably, I and I' can be between about 10 and about 20 inches in length. Most preferably, I and I' are about 14 inches in length. The length J represents the distance between the beginning of the fluid-collection reservoir and the beginning of the side opening of the fluid-collection pouch. J and J' may or may not be the same length. Preferably, J and J' can be between about 1 and about 10 inches in length, alternatively from about 5 inches to about 7 inches. Most preferably, J and J' are about 6 inches in length. The length K represents a portion of the fluid-collection pouch where one of the reservoirs is located. K and K' may or may not be the same length. Preferably, K and K' can be between about 5 and about 15 inches in length. Most preferably, K and K' are about 13 inches. In FIG. 3, the length G represents the length of the side openings of the fluid-collection pouch. G can be between about 10 and about 30 inches in length, alternatively between about 15 and about 25 inches. Preferably, G is about 18 inches. The length H represents the length of the top opening of the fluid-collection pouch. H can be between about 10 and about 30 inches in length, alternatively between about 15 and about 25 inches. Preferably, H is about 17.5 inches. In FIG. 5, the symbol L represents the length of the top opening of the fluid-collection pouch and can be between about 10 and about 20 inches, alternatively between about 12 to about 16 inches. Preferably, L can be about 14 inches. The symbol M represents the length of the side opening of the fluid-collection pouch and can be between about 8 and about 16 inches in length, alternatively about 10 to about 14 inches. Preferably, M is about 12.5 inches.

In an embodiment employing more than one pouch, each with one or more reservoirs, the fluid-collection pouch dimensions can be about 12 to about 22 inches wide at the opening of the pouch and about 14 to about 24 inches deep, alternatively, about 16 to about 20 inches wide and about 17 to about 21 inches deep, alternatively about 18 inches wide and about 19 inches deep.

In an embodiment employing one pouch with multiple reservoirs, the fluid-collection pouch dimensions can be about 30 to about 70 inches wide along the latitudinal axis of the drape and about 20 to about 60 inches long along the longitudinal axis of the drape, alternatively, about 40 to about 60 inches wide and about 30 to about 50 inches long, alternatively about 45 to about 55 inches wide and about 35 to about 45 inches long, alternatively about 52 inches wide and about 41 inches long.

One or more fluid collection pouches are preferably attached to the exterior surface of the drape and each pouch is in fluid communication with the cranial surgical site fenestration when the drape and pouch are in their normal operational position on a patient. In a preferred embodiment, a fluid collection pouch 10 is disposed on at least two sides of the cranial region fenestration, alternatively at least three sides 11, 12, 13, alternatively on all sides of the fenestration. In some embodiments shown in the Figures, one fluid-collection pouch is disposed on three sides of the cranial region fenestration and thereby surrounds a majority (actually at least about three-quarters) of the perimeter of the cranial region fenestration.

One or more fluid-collection pouches preferably contain a screen or filter 7 which allows fluids to flow into the pouch opening and down to the reservoir at the bottom of the pouch, but inhibits any solids from reaching the reservoir. The filter 7 can be comprised of any semi-permeable material or non-permeable material with irrigation holes or slits. Preferably, the filter is comprised of a plastic or a plastic coated metal. Most preferably, the filter is comprised of polyethylene.

In a preferred embodiment, malleable strips 14 may be located at or inserted into the top opening of each fluid-collection pouch or reservoir to maintain each pouch in an open configuration (i.e., able to receive fluids). These malleable strips 14 can be constructed from a number of materials such as plastic, metal or plastic coated metal.

In another preferred embodiment, an access port 8 is located in each fluid-collection reservoir. The access port would enable the medical staff to take fluid samples from the fluid-collection reservoir. Further, it is contemplated to have connection fixtures on the access port 8 to facilitate a connection with tubing, for example. Each access port has a cap when the medical staff desires the access port to remain closed.

In a further preferred embodiment, channels (such as rails or flaps) may be included on the exterior surface of the drape to control fluid control into the fluid-collection pouch(es). The channels can be positioned so as to channel fluid from the fenestration to a fluid-collection pouch. The channels can be attached to the exterior surface of the sheet. The channels may be located alongside but spaced from the fenestration in the cranial region such that when the exterior surface and the pouch are in their normal operational position, fluid runoff from the fenestration in the cranial region flows through a channel into an opening of a pouch. Methods of channeling fluids in a surgical drape have been disclosed in U.S. Pat. Nos. 4,890,628 and 4,169,472 and are hereby incorporated by reference.

Unlike other designs, the present drapes do not have separate pieces which can become misaligned or detached thereby creating a risk of fluid spilling over onto other areas of the patient, the surgical team or the operating floor. Such hazards are especially apparent when the surgical procedure requires frequent movement and repositioning of the patient.

The present cranial surgical drapes can be provided as sterile drapes. Sterile means essentially free from live bacteria or other live microorganisms. The process of sterilization is known in the art and examples include, but are not limited to, steam sterilization and ethylene oxide sterilization. The sterile drape can be provided in a package for containing the sterile surgical drape and optionally other items and for maintaining the sterility of the drape.

Some of the advantages of the present cranial surgical drapes stem from the unique fluid collection pouch configuration. The configuration allows the surgeon to work without concern of re-draping or changing the existing draping configuration. Moreover, embodiments having an additional fenestration in the thoracic region allows the surgeon to perform subcutaneous placement of cranial bone grafts which is often performed in conjunction with certain cranial surgeries.

What is claimed is:

1. A cranial surgical drape to cover a patient during surgery, the drape comprising:

- a sheet having an interior surface arranged to contact a cranial region of the patient and an exterior surface arranged to face away from the patient;
- a cranial region fenestration in the cranial region, wherein the sheet has a perimeter that defines the cranial region fenestration; and
- a fluid-collection pouch on the exterior surface of the sheet adjacent to and surrounding a majority of the perimeter defining the cranial region fenestration, wherein:

- the fluid-collection pouch is fastened to the exterior surface and is in fluid communication with the cranial region fenestration,
- the fluid-collection pouch comprises at least three reservoirs,
- each of the at least three reservoirs is on a different side of the cranial region fenestration, and
- each of the at least three reservoirs comprises widths such that a width at a bottom of a given reservoir is narrower than a width at a top of the given reservoir.

2. The drape of claim 1, wherein a different access port is located in each of the at least three reservoirs.

3. The drape of claim 1, wherein each of the at least three reservoirs comprises a triangular shape.

4. The drape of claim 1, wherein the drape comprises an absorbent layer on the exterior surface.

5. The drape of claim 4, wherein the absorbent layer comprises pulp-based non-woven fabric.

6. The drape of claim 1, wherein the drape comprises spunbond polypropylene.

7. The drape of claim 1, wherein the drape comprises an adhesive layer on the interior surface of the drape surrounding the cranial region fenestration.

8. The drape of claim 1, wherein the fluid-collection pouch is comprised of a polypropylene.

9. The drape of claim 1, wherein the fluid-collection pouch contains a filter.

10. The drape of claim 1, wherein the drape further comprises a cord fastener.

11. The drape of claim 1, wherein the drape further comprises one or more channels to provide fluid communication between the cranial region fenestration and the fluid-collection pouch.

12. The drape of claim 1, wherein the drape is a sterile drape.

13. A packaged sterile surgical drape comprising the sterile drape of claim 1 and a package that contains the sterile surgical drape and maintains the sterility of the drape.

* * * * *